United States Patent
Danley

(10) Patent No.: US 7,470,057 B2
(45) Date of Patent: Dec. 30, 2008

(54) DIFFERENTIAL SCANNING CALORIMETER SENSOR AND METHOD

(75) Inventor: Robert L. Danley, Collingswood, NJ (US)

(73) Assignee: Waters Investments Limited, New Castle, DE (US)

( * ) Notice: Subject to any disclaimer, the term of this patent is extended or adjusted under 35 U.S.C. 154(b) by 0 days.

(21) Appl. No.: 11/843,225

(22) Filed: Aug. 22, 2007

(65) Prior Publication Data

US 2008/0052032 A1 Feb. 28, 2008

Related U.S. Application Data

(60) Provisional application No. 60/839,673, filed on Aug. 24, 2006.

(51) Int. Cl.
*G01N 25/00* (2006.01)
*G01K 17/00* (2006.01)

(52) U.S. Cl. ............................. 374/13; 374/12; 374/31

(58) Field of Classification Search ............ 374/10, 374/11, 12, 13, 31
See application file for complete search history.

(56) References Cited

U.S. PATENT DOCUMENTS

| | | | | |
|---|---|---|---|---|
| 3,554,002 | A * | 1/1971 | Harden et al. ............ | 374/13 |
| 4,095,453 | A * | 6/1978 | Woo ........................ | 374/13 |
| 5,033,866 | A | 7/1991 | Kehl et al. | |
| 5,224,775 | A * | 7/1993 | Reading et al. ........... | 374/11 |
| 5,288,147 | A | 2/1994 | Schaefer et al. | |
| 5,439,291 | A * | 8/1995 | Reading .................... | 374/11 |
| 5,711,604 | A * | 1/1998 | Nakamura ................. | 374/44 |
| 5,788,373 | A * | 8/1998 | Huetter et al. ............ | 374/10 |
| 5,842,788 | A * | 12/1998 | Danley et al. ............. | 374/12 |
| 6,431,747 | B1 | 8/2002 | Danley | |
| 6,488,406 | B2 | 12/2002 | Danley | |
| 6,508,585 | B2 * | 1/2003 | Nakamura et al. ........ | 374/12 |
| 6,530,686 | B1 * | 3/2003 | Nakamura ................. | 374/11 |
| 6,583,391 | B2 * | 6/2003 | Jorimann et al. ......... | 219/497 |
| 6,641,300 | B1 * | 11/2003 | Lacey et al. .............. | 374/31 |
| 7,371,006 | B2 * | 5/2008 | Schick ..................... | 374/10 |
| 2003/0072348 | A1 * | 4/2003 | Danley ..................... | 374/31 |
| 2003/0165179 | A1 * | 9/2003 | Danley ..................... | 374/31 |

OTHER PUBLICATIONS

G.W.H. Hohne, W. Hemminger, H.J. Flammersheim, "Differential Scanning Calorimetry", Springer, Berlin, 1996, pp. 21-40.
R.L. Danley, "New Heat Flux DSC Measurement Technique", Elsevier, Thermochimica Acta 395 (2003), pp. 201-208.
S.L. Boersma, "A Theory of Differential Thermal Analysis And New Methods of Measurement and Interpretation", Journal of The American Ceramic Society, Delft, Holland, 1955, vol. 38, No. 8, pp. 281-284.

(Continued)

*Primary Examiner*—Gail Verbitsky
*Assistant Examiner*—Mirellys Jagan
(74) *Attorney, Agent, or Firm*—Aslan Baghdadi; Paul, Hastings, Janofsky & Walker LLP

(57) ABSTRACT

A sensor for a heat flux differential scanning calorimeter in which the differential temperatures are measured between locations external to the regions of heat exchange between the sensor and sample containers. The measured differential temperatures respond to the magnitude of the heat flow rate between the sensor and the sample and reference containers and are rendered insensitive to variations in the magnitude and distribution of thermal contact resistance between the sensor and the containers.

12 Claims, 5 Drawing Sheets

OTHER PUBLICATIONS

A. Savitzky, M.J.E. Golay "Smoothing and Differentiation of Data by Simplified Least Squares Procedures", Analytical Chemistry, Connecticut, Jul. 1964, vol. 36, No. 8, pp. 1627-1639.

A. Savitzky, M.J.E. Golay, "Comments on Smoothing and Differentiation of Data by Simplified Least Square Procedure", Analytical Chemistry vol. 44, No. 11, Sep. 1972, pp. 1906-1909.

* cited by examiner

DIFFERENTIAL SCANNING CALORIMETER SENSOR AND METHOD

This application claims the benefit of U.S. Provisional Application No. 60/839,673, filed Aug. 24, 2006, which is herein incorporated by reference in its entirety.

BACKGROUND

1. Field of the Invention

Embodiments of the present invention relate to differential scanning calorimetry. More particularly, embodiments of the present invention relate to an apparatus and method for measuring sample heat flow rate in a differential scanning calorimeter.

2. Background of the Invention

Differential scanning calorimetry is an analytical technique in which the rate of heat flow to and from a sample under analysis is measured while the sample is exposed to a dynamic temperature program. The temperature program may be comprised of constant heating or cooling rate segments combined with isothermal segments, all of which may have superposed temperature modulation of various forms. The temperature modulation can be periodic or aperiodic. Differential scanning calorimetry techniques using temperature modulation are referred to by a variety of names including modulated DSC, temperature modulated DSC, and dynamic DSC.

At this time, there are two different types of DSC instruments in commercial production. One type of DSC instrument operates on the principle of compensation of the thermal effect, and is typically referred to as power compensation DSC. The second type of DSC instrument operates on the principal of measurement of a temperature difference, and is typically referred to as heat flux DSC.

In general, DSC instruments that operate on the heat flux principle use the following equation to obtain the heat flow rate from the measured temperature difference:

$$\dot{q} = \frac{\Delta T}{K(T)} \tag{1}$$

where $\Delta T$ is the measured temperature difference and $K(T)$ is a temperature dependent proportionality factor that is characteristic of the particular calorimeter in question. Dimensionally, the proportionality factor $K(T)$ must have the units of a thermal resistance, i.e., temperature divided by energy per unit of time, for example), ° C./joule/second, i.e., ° C./watt. The physical significance of the proportionality constant is that it represents the effective thermal resistance of the heat flow path between the sample and the controlled temperature enclosure or surroundings of the calorimeter. In the case of a differential scanning calorimeter, the temperature difference is measured between two nominally identical sample and reference calorimeters where the sample under analysis is placed in a sample container that is installed in the sample calorimeter, and an inert reference material is placed in the reference calorimeter. Despite its near universal application, equation (1) may be shown to be a great over-simplification of the actual sample heat flow rate. See, for example, G. W. H. Höhne, W. Hemminger, H. J. Flammersheim, "Differential Scanning Calorimetry," Springer, Berlin, 1996, pp. 21-33, which is hereby incorporated by reference herein in its entirety.

As shown in R. L. Danley, Thermochim. Acta 395 (2003) 201 and disclosed in U.S. Pat. No. 6,431,747 to Danley, which are hereby incorporated by reference herein in their entirety, a heat flow rate measurement method has been developed that avoids many of the assumptions implicit in equation (1). However, this heat flow rate measurement requires the measurement of two temperature differences and a calibration method to measure the heat transfer characteristics of the individual sample and reference calorimeters. In that method, the sample and reference heat flow rates are measured separately using the following equations:

$$\dot{q}_s = \frac{\Delta T_0}{R_s} - C_s \dot{T}_s \tag{2}$$

$$\dot{q}_r = \frac{\Delta T_0 + \Delta T}{R_r} - C_r(\dot{T}_s - \Delta \dot{T}) \tag{3}$$

where $\Delta T_0$ is a second temperature difference measured across the thermal resistance of the sample calorimeter, $T_s$ is the temperature of the sample calorimeter, $R_s$ and $R_r$ are the thermal resistances of the sample and reference calorimeters, and $C_s$ and $C_r$ are the heat capacities of the sample and reference calorimeters. The thermal resistances and heat capacities of the calorimeters are determined from the calibration method mentioned above. The difference between the sample and reference calorimeter heat flow rates may be taken, resulting in a sample heat flow rate measurement that includes differences between the thermal resistances and heat capacities of the sample and reference calorimeters and which accounts for heating rate differences between the two calorimeters:

$$\dot{q} = -\frac{\Delta T}{R_r} + \Delta T_0 \left( \frac{1}{R_s} - \frac{1}{R_r} \right) + (C_r - C_s)\frac{dT_s}{dt} - C_r \frac{d\Delta T}{dt} \tag{4}$$

It should be noted that the first term of heat flow rate equation (4) is essentially the same as equation (1).

Alternatively, if the effects of heating rates and mass differences between the sample and reference containers are taken into account, the following heat flow rate equation may be used:

$$\dot{q} = \dot{q}_s - \dot{q}_r \left( \frac{m_{ps} \dot{T}_{ps}}{m_{pr} \dot{T}_{pr}} \right) \tag{5}$$

where $m_{ps}$ and $m_{pr}$ are the masses of the sample and reference containers and $T_{ps}$ and $T_{pr}$ are the temperatures of the sample and reference containers, which are found from:

$$T_{ps} = T_s - \dot{q}_s R_p \tag{6}$$

$$T_{pr} = T_r - \dot{q}_r R_p \tag{7}$$

where $T_s$ is the temperature of the sample calorimeter, $T_r$ is the temperature of the reference calorimeter, and $R_p$ is the thermal contact resistance between each calorimeter and its sample container.

The precision of the heat flow rate measurement depends on how repeatable the measured signals are for a given sample heat flow rate. Boersma (see, S. L. Boersma, J. Am. Ceram. Soc. 38 (1955) 281) found that by mounting the temperature sensors within the sample holders rather than within the sample material the precision of a differential thermal analysis apparatus was greatly improved, enabling quantitative heat flow rate measurements. The measured temperature and temperature differences depend upon the position of the temperature sensors relative to the sample and reference and to other components of the calorimeter.

Thermal contact resistance is the impediment to the flow of heat across the interface between two solid surfaces. Thermal resistance is due to form imperfections in the two mating surfaces resulting in limited direct contact between them. Thus, heat exchange between two solid surfaces that nominally contact each other over a given area is by conduction between regions in the given area where the two surfaces are in direct contact, and by conduction through the gas within the interstitial spaces between the regions of direct contact. Convective heat exchange generally does not occur because the interstitial spaces are small and the viscosity of the gas is sufficiently large that it prevents motion of the gas due to temperature differences between the surfaces. Radiation heat exchange occurs between the two contact surfaces but is typically insignificant because the temperature differences are generally quite small.

In DSC, there are two contact resistances that are of concern. The first contact resistance of interest in DSC is that between the sample and its container, as well as the reference material, if used, and its container. The second contact resistance of interest in DSC is that between the containers and the calorimeters Given that the sample size and shape may vary greatly between samples to be analyzed, the thermal contact resistance between the sample and its container may not be easily controlled. Because the form imperfections of any given sensor and container mating surface differ for different containers or sensors, the contact resistance between any container and sensor combination is different from that of another container/sensor combination and also differs when the relative orientation of the container and sensor surfaces is changed for the same container/sensor combination. Thus, the thermal contact resistance between a DSC sensor and the sample and reference containers installed on the sensor changes whenever a new container is introduced, or even when the same sample container is removed from the DSC and subsequently replaced. These changes result in a different distribution of heat flow between the two surfaces and a different temperature distribution within the container and the calorimeter. If the temperature differences and the temperatures of the calorimeter are measured beneath the region of contact between the pan and sensor, their values are affected by the changes in magnitude and distribution of contact resistance between the surfaces.

U.S. Pat. No. 3,554,002 to Harden, et al. ("Harden"), discloses a differential thermal analysis sample cell in which wires are connected to a sample cell assembly constructed of one of a pair of thermocouple materials. Three wires are joined to the cell assembly, one of which is of the same thermoelectric material as the cell, while the other two are of the opposite material of the thermocouple pair. Each of the wires of the opposite material to the cell material are connected in a position that is axisymmetric with respect to each of a sample and a reference location within the cell, the sample and reference having a cylindrical form. The connection of the wire of like material to the cell assembly may be located anywhere on the cell assembly. A differential temperature is measured between the two wires of opposite thermoelectric composition to the cell, and a temperature is measured between the wire of like thermoelectric composition to the cell material and the wire of opposite thermoelectric composition to the cell material that is attached axisymmetrically with respect to the sample position. Thus, the differential temperature is measured between the two points of attachment of wires of opposite thermoelectric material to the cell material. The measured temperature difference depends on the magnitude of the heat flow rates between the sample and reference and the cell and on the position of the sample and reference materials within the cell and the distribution of thermal contact resistance between those materials and the cell. The temperature measured between the wire attached to the axisymmetric position of the sample position and the wire of like thermoelectric composition attached to the sample cell is taken as the sample temperature. Using a differential thermal analysis apparatus of the type disclosed in Harden, sample heat flow rate may be measured using equation (1).

U.S. Pat. No. 4,095,453 to Woo ("Woo") discloses a heat flux differential scanning calorimeter that uses a planar thermoelectric disk, with a disk type area thermocouple beneath each of the sample and reference positions of the calorimeter. These two thermocouples are connected to measure the differential temperature between the sample and reference positions. The sample heat flow rate is obtained from the instrument using equation (1). The claimed advantage of the apparatus disclosed in Woo is the improved reproducibility of the heat flow rate signal by using these area thermocouples as opposed to point thermocouples as used in Harden. According to Woo, this reduces the effects of variations in the differential temperature measurement resulting from variations in the positions of the sample and reference containers within the apparatus and variations in thermal contact resistance between the apparatus and the sample and reference containers.

U.S. Pat. No. 6,431,747 to Danley ("Danley") discloses a heat flux differential scanning calorimeter sensor using a disk type thermocouple system similar to that of Woo to improve reproducibility of the heat flow rate signal and that uses the heat flow rate measurements of equations (2) through (7). In addition, the DSC of Danley has the advantage of greatly improving separation of the sample and reference heat flow signals over the apparatus disclosed in Harden and Woo.

In Harden, Woo, and Danley, the differential temperature is measured using a single differential thermocouple. However, the differential temperature may also be measured using a thermopile that consists of a series of thermocouples connected in series and arranged so that every other thermocouple junction is located within one of a sample and a reference region between which the differential temperature is to be measured. The advantage of using a thermopile over using a single thermocouple is that a larger electrical signal may be generated using a thermopile.

However, thermopile sensors are in general more complex and more difficult to manufacture. Moreover, in reality, due to the available choice of thermocouple materials and other design factors, the actual advantages of using thermopiles is generally less than otherwise might be expected. Differences notwithstanding, all of the above comments that have been made with respect to the method of heat flow rate measurement and sample and reference container position and contact resistance apply equally to DSC apparatus using thermopile differential temperature sensing.

U.S. Pat. No. 5,033,866 to Kehl, et al. ("Kehl"), discloses a thermopile thermal analysis sensor that may be used to measure sample heat flow rate using the method of equation (1) in which thermoelectric materials are deposited on a ceramic substrate using thick film processes such as those employed in the manufacture of integrated circuits and hybrid electronic devices. The temperature difference is measured between a circular region beneath the sample position of the sensor and a circular region beneath the reference position of the sensor.

U.S. Pat. No. 5,288,147 to Schaefer et al. ("Schaefer") discloses a differential thermal analysis sensor that incorporates two thermopiles that may be used to measure sample heat flow rate using either equation (1) or the method of equations (2) through (7). As with the apparatus disclosed in Kehl, the thermopiles are formed using thick film processes. However, unlike Kehl, the apparatus disclosed in Schaefer uses two separate thermopiles that measure the temperature difference between the sample position and a second region of the sensor located within a portion of the sensor assembly that is attached to the DSC enclosure and between the reference position and the second region of the sensor.

SUMMARY OF THE INVENTION

In an embodiment of the present invention, a sensor for a heat flux differential scanning calorimeter is configured so that the differential temperatures are measured between locations external to the regions of heat exchange between the sensor and sample containers. The measured differential temperatures respond to the magnitude of the heat flow rate between the sensor and the sample and reference containers and are rendered insensitive to variations in the magnitude and distribution of thermal contact resistance between the sensor and the containers. Heat flow rate measurements made using the invention have increased precision.

In one embodiment, the present invention is a differential scanning calorimeter sensor. The differential scanning calorimeter sensor includes a base having a sample thin wall part and a reference thin wall part. A sample platform is joined to the base on a top surface of the sample thin wall part for supporting a sample container. A reference platform is joined to the base on a top surface of the reference thin wall part for supporting a reference container. A sample thermocouple wire is attached to the sample platform to measure the temperature of the sample, and a reference thermocouple wire attached to the reference platform to measure the temperature of the reference, even if no physical reference is present. A first base thermocouple wire attached is to the base and a second base thermocouple wire attached is to the base.

In another embodiment, the present invention is a method for determining heat flow rate using a differential scanning calorimeter. The method includes placing a sample in a sample container, placing the sample container on a sample platform placing the reference container on a reference platform. In addition, the method includes applying a temperature program to the sample through the sample platform and sample container and applying a temperature program to the reference through the reference platform and reference container. In addition, the method includes measuring a differential temperature using a differential scanning calorimeter sensor wherein the differential temperature is measured externally to the area of thermal contact between the sensor and the sample and reference containers; and determining a heat flow rate in accordance with the measured differential temperature.

DETAILED DESCRIPTION OF THE INVENTION

In conventional differential scanning calorimeters ("DSCs"), the measured temperature differences may be affected not only by the magnitude of the heat flow rate between the sample and the calorimeter, but also by the magnitude and distribution of thermal contact resistance between the sample and reference containers and the DSC. Embodiments of the present invention, in contrast, allow performing heat flux DSC in which the measured temperature differences are rendered substantially insensitive to variations of the magnitude and distribution of thermal contact resistance between the sample and reference containers and the DSC.

In one embodiment of the present invention, a sensor is built in which the differential temperature measurements are made on regions of the thermal resistances of the sensor wherein the thermocouple junction is located such that all heat that flows between the sample and reference sensors and the sample and reference containers flows through the sample and reference thermocouple junctions. Thus, the measured sample heat flow rate, whether measured using the method of equation (1) or equations (2) through (7) depends essentially on the magnitude of the sample heat flow rate, and is largely unaffected by variations in the magnitude and distribution of thermal contact resistance between the sample and reference containers and the DSC.

Figure 1:
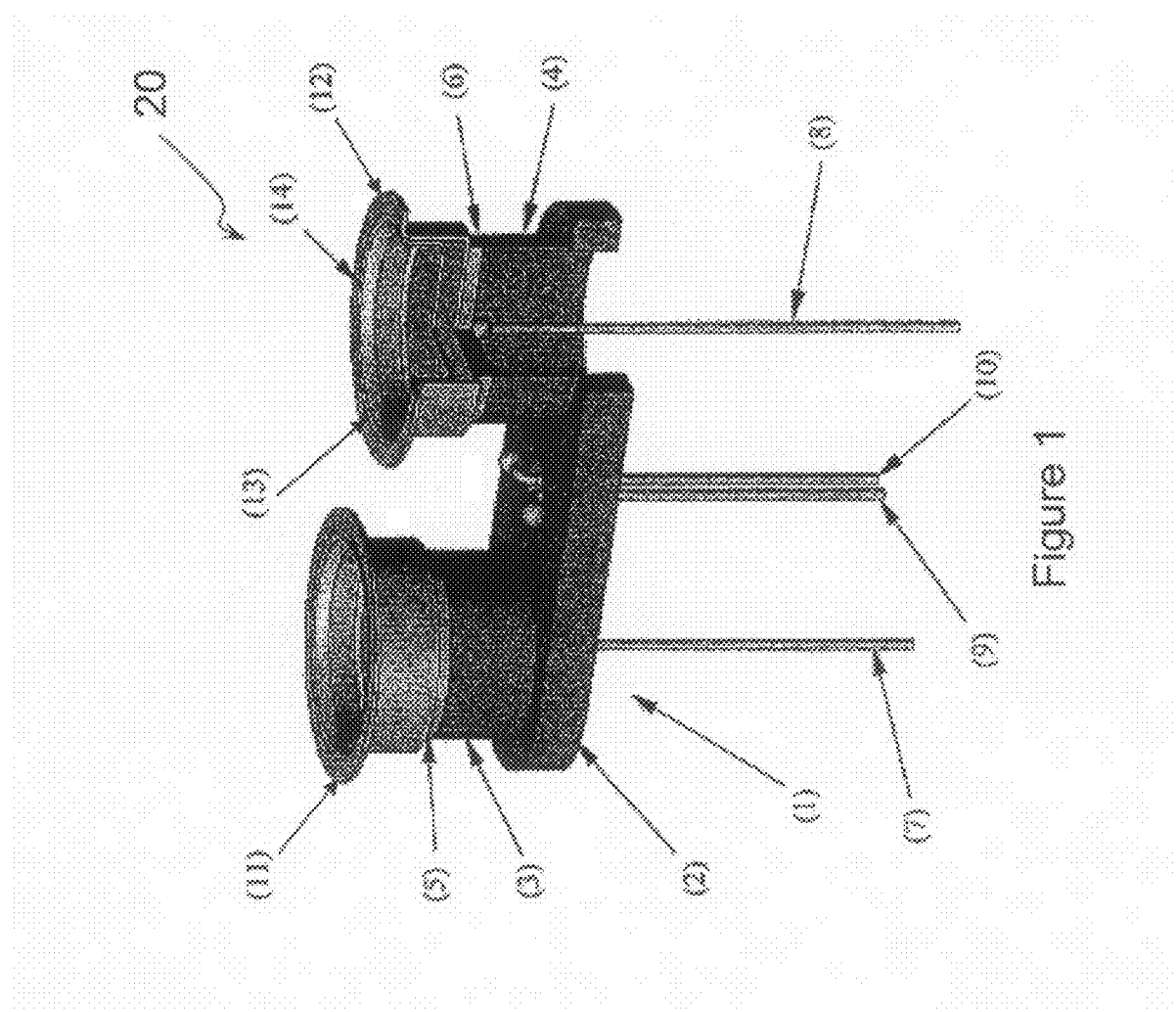
FIG. 1 is a schematic diagram of a DSC sensor according to an embodiment of the present invention.

FIG. 1 is a schematic diagram of a differential scanning calorimeter sensor 20 according to an embodiment of the present invention in which the thermocouple junctions are formed and located in a manner that reduces the variation of differential temperature signals due to variations in contact resistance between the sample and reference containers and the sensor. For clarity, a section has been taken through the sensor and sample container to expose internal features. Sensor 20 may be used to measure the sample heat flow rate using the method of equation (1) or of equations (2) through (7).

In one embodiment of the present invention, a body 1 of sensor 20 comprises a base 2 and two thin wall cylindrical parts, a reference thin wall part 3 and a sample thin wall part 4. Thin wall parts 3 and 4 can be any desired shape, but are preferably cylindrical. In one embodiment of the present invention, base 2 and thin wall parts 3 and 4 are made of one of the alloys of the thermocouple pair. For example, in one embodiment of the present invention, the metallic thermocouple pair type E, chromel vs. constantan, is used. Other available metallic thermocouple pairs could also be used, such as type K: chromel vs. alumel, type J: iron vs. constantan and type T: copper vs. copper-nickel. An advantage of a type B, chromel vs. constantan, metallic thermocouple pair over other metallic thermocouple pairs is that if has the highest thermoelectric output, thereby providing the largest electrical signal for a given temperature difference.

Base 2 is a relatively thick member with a flat lower surface to facilitate installing sensor 20 in a DSC enclosure. According to one embodiment of the present invention, the thickness of base 2 ranges from 0.025" to 0.100", with a preferred thickness of 0.050". Thin wall parts 3 and 4 form thermal resistances $R_s$, and $R_r$ across which temperature differences $\Delta T$ and $\Delta T_0$ are measured. According to one embodiment of the present invention, the thickness of thin wall parts 3 and 4 ranges from 0.003" to 0.015" with a preferred thickness of 0.006".

Sensor 20 also includes a reference platform 5 and a sample platform 6. Reference platform 5 and sample platform 6 are made of the other material of the thermocouple pair (the material of the pair not used to make base 2 and thin wall parts 3 and 4). Reference platform 5 is attached to the top end of thin wall part 3, and sample platform 6 is attached to the top end of thin wall part 4.

Reference container 11 and sample container 12 including their respective samples are placed on the top sides of reference and sample platforms 5 and 6, respectively, of sensor 20. As shown in FIG. 1, sample container 12 includes a container 13 and a cover 14. Reference container 11 has a similar container/cover structure. In operation, a sample (not shown) is placed in container 13 of sample container 12, and a reference, if used, is placed in a container of reference container 11. However, in typical use, reference container 11 is kept empty. Containers 11 and 12 are typically made of a high thermal conductivity material such as aluminum that helps to ensure that the entire sample is at a uniform temperature to improve temperature precision of any physical or chemical process that occurs within the sample.

As depicted in FIG. 1, a thermocouple wire 7 is attached to the underside (the side opposite the top side that supports reference container 11) of reference platform 5 and a thermocouple wire 8 is attached to the underside (the side opposite the top side that supports sample container 12) of sample platform 6. Thermocouple wires 7 and 8 are made of the same alloy as platforms 5 and 6. Although elements 7 and 8 are depicted as wires, elements 7 and 8 can also be rods or other solid forms comprising the same alloy as platforms 5 and 6. As discussed further below, the placement of elements 7 and 8 on the respective undersides of platforms 5 and 6 ensures that measurements of differential temperatures are external to the area of thermal contact between the sensor and the containers (top side of platforms 5 and 6). In an embodiment of the present invention thermocouple wire 7 is attached at the center of the underside of reference platform 5, and thermocouple wire 8 is attached at the center of the underside of sample platform 6. However, because it does not affect performance of sensor 20, the position of the attachment of wires 7 and 8 to the underside of their respective platforms is not important.

A wire 9 is attached in the center region of base 2 of sensor 20. A wire 10 is also attached in the center region of base 2 of sensor 20. Wire 9 is made of the same alloy as base 2. Wire 10 is made of the same alloy as platforms 5 and 6.

In operation, sample platform-to-reference differential temperature, $\Delta T$, is measured between wires 7 and 8 and sample platform-to-sensor base differential temperature $\Delta T_0$ is measured between wires 8 and 10. The temperature of base 2 is measured between wires 9 and 10. The temperature of base 2 is used to control the temperatures of the DSC in a well-known manner, and is controlled to follow a desired temperature program in a well-known manner. Sample calorimeter temperature $T_s$ is measured between wires 8 and 9. Sample calorimeter temperature can be reported as the sample temperature for analysis of the experiment. When the method of equations (5) through (7) and (2) and (3) is used, sample pan temperature $T_{ps}$, as calculated using equations (2) and (6) may be reported as the sample temperature.

The measured differential temperature $\Delta T = T_s - T_r$, as used hereinafter, is the difference between the average temperature at the interface between the platform and the thin wall cylinder of the sensor body on the sample side, and the average temperature of the interface between the platform and the thin wall cylinder of the sensor body on the reference side. In brief, $\Delta T$ is also referred to as the differential temperature measured between the sample and reference platforms (or sample-to-reference differential temperature). Unlike with conventional DSC sensors, a DSC sensor according to an embodiment of the present invention locates the junctions of the differential temperature measurements such that all heat that flows between the sample and reference calorimeters and their respective containers flows through the sample and reference calorimeter thermocouple junctions. Thus, the measured differential temperatures are essentially unaffected by variations in magnitude and distribution of contact resistance between the containers and the sensor. As a result, differential temperatures measured by a sensor according to an embodiment of the present invention will depend primarily on the magnitude of the heat flowing between the sensor and the sample containers. Thus, the precision of the heat flow rate measurement using a DSC sensor according to an embodiment of the present invention is improved over conventional DSC instruments.

DSC sensor 20 may be fabricated using any convenient process for joining thermocouple alloys. Such processes include welding, soldering and brazing, and solid-state welding joining processes, including diffusion welding and deformation welding. The preferred joining methods for embodiments of the present invention are resistance welding for attaching the wires, and diffusion welding, also called diffusion bonding, for joining the sample and reference platforms to the sensor body.

Diffusion welding is a process where the faying surfaces of the two materials to be joined are ground or polished so that they are very flat and smooth to ensure uniform intimate contact between them. During the diffusion welding process, the faying surfaces are clamped together under high pressure and heated in a furnace under controlled atmosphere that prevents or reduces oxidation to a temperature that is typically in the vicinity of 60 to 75 percent of the melting point of the point of the lower melting point of the two materials. Pressure and temperature is maintained for some period of time while the two materials diffuse into one another across the interface. Upon cooling and release of the clamping pressure, the two materials are inseparably joined into a single piece.

Figure 2:
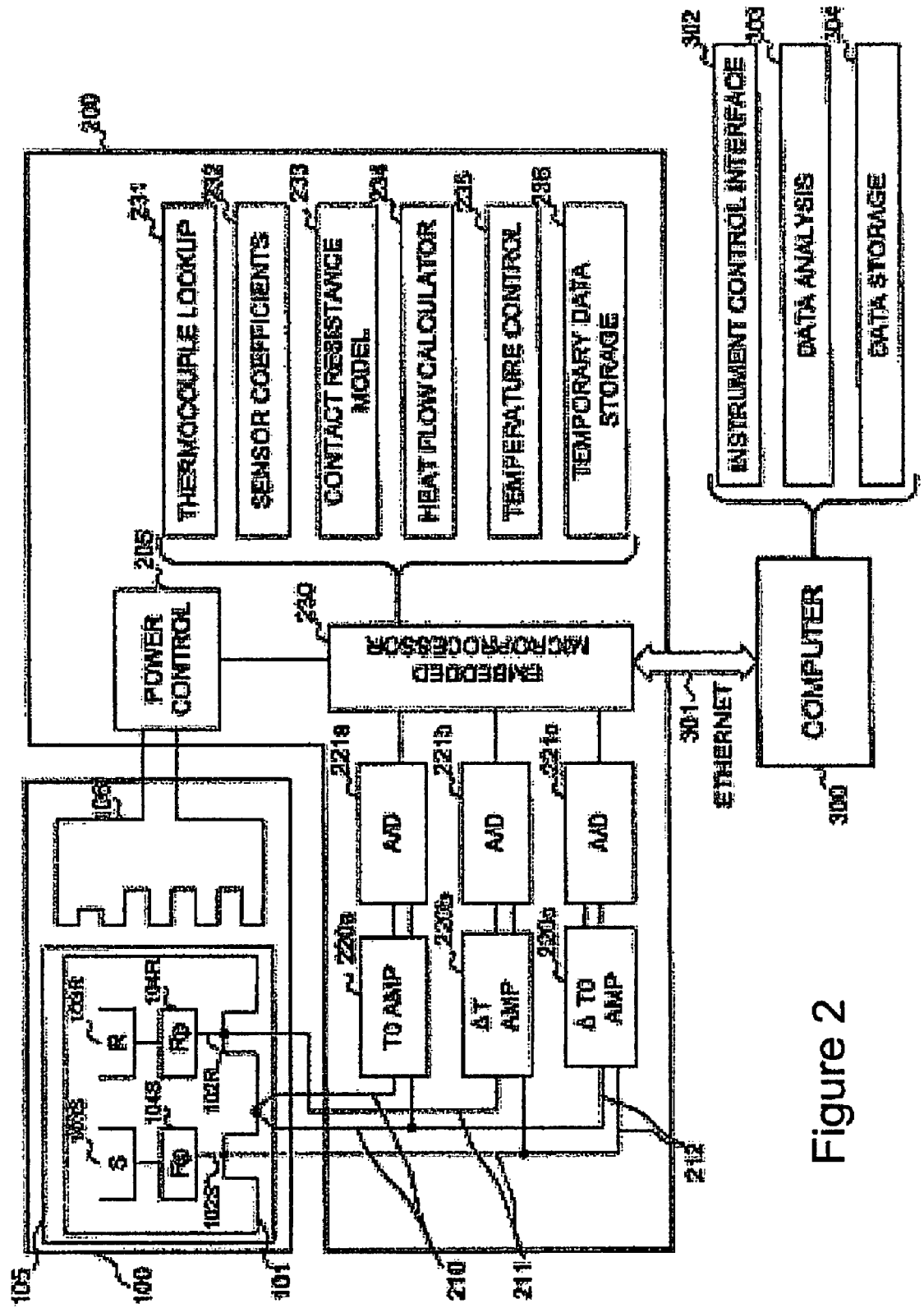
FIG. 2 is a schematic diagram of a DSC instrument according to an embodiment of the present invention.

FIG. 2 is a schematic diagram of a DSC instrument according to an embodiment of the present invention. In the embodiment of the present invention illustrated in FIG. 2, the DSC comprises three main components, a DSC cell 100, a DSC module 200 and a computer 300. DSC cell 100 comprises a sensor assembly 101 with sample position 102S and a reference position 102R. A sample within a sample pan 103S and a reference within a reference pan 103R are placed on the sample and reference positions. In alternative uses, the reference pan is kept empty. Heat is exchanged between each of the pans and its sensor position by a sample thermal contact thermal resistance 104S and a reference thermal contact thermal resistance 104R. Sensor assembly 101 is installed within an enclosure 105 heated by heating element 106. In one embodiment of the present invention, DSC cell 100 is coupled to a heat sink or other cooling apparatus to allow it to operate at low temperatures. This allows extension of its operating range and enhances the rate of cooling. The temperature of the DSC cell 100 is controlled via power control 205, according to instructions received from embedded microprocessor 230.

DSC module 200 includes $T_0$, $\Delta T$ and $\Delta T_0$ amplifiers 220a, 220b and 220c, respectively, which receive input from thermocouples 210, 211 and 212 as shown in FIG. 1. Thermocouple 210 measures the temperature of the base, thermocouple 211 measures the difference between the reference and sample calorimeter temperatures, and thermocouple 212 measures the difference between the base and sample calorimeter temperatures. The output signals of the $T_0$, $\Delta T$, and $\Delta T_0$ amplifiers are converted from analog to digital signals by A/D converters 221a, 221b and 221c. The output of the A/D converters is provided to embedded microprocessor 230. Embedded microprocessor 230 comprises thermocouple lookup application 231, sensor coefficient application 232, contact thermal resistance model 233, heat flow calculation 234, temperature control application 235 and temporary data storage 236.

Thermocouple Lookup 231 is a program resident in embedded microprocessor 230 that converts the digital signal representing the output signal of the $T_0$ thermocouple to a temperature. The temperature of the terminals of the $T_0$ thermocouple wire is measured by a thermistor, and that temperature is converted to the equivalent voltage of a thermocouple at that temperature. The equivalent thermocouple voltage is summed with the output voltage of the $T_0$ thermocouple. The resultant reference junction compensated voltage is converted to temperature by using a thermocouple lookup table 231 of temperature versus voltage that is based on NIST monograph 175.

Sensor Coefficients 232 is a program resident in embedded microprocessor 230 that supplies the sensor coefficients ($R_s$, $R_r$, $C_s$, $C_r$) used in the heat flow calculation. The temperature of the DSC cell as indicated by the $T_0$ thermocouple is used to determine the appropriate value for each of the coefficients. Sensor coefficients can be generated using the calibration procedures of U.S. Pat. No. 6,431,747, and saved in the module in tabular form. The program supplies the sensor coefficients to heat flow calculator 234.

Contact Resistance Model 233 is a program resident in the embedded microprocessor that calculates the pan contact thermal resistance using the thermal contact thermal resistance model equation disclosed in U.S. Pat. No. 6,431,747.

Heat Flow Calculator 234 is a program resident in embedded microprocessor 230 that calculates heat flow rate using the methods described herein. Sensor coefficients required by the program are supplied by sensor coefficient program 232 and pan contact thermal resistances needed by the program are supplied by contact thermal resistance model program 233.

Temperature Control 235 is a program resident in embedded microprocessor 230 that determines the power to be supplied to DSC heater 106. In one embodiment of the present invention, Temperature Control program 235 operates according to a PID (proportional-integral-differential) control scheme.

Temporary Data Storage 236 is non-volatile RAM within module 200 that stores the results of an experiment during the experiment.

Embedded microprocessor 230 is in communication over, e.g., an ethernet network 301, with computer 300. Computer 300 comprises instrument control interface 302, data analysis module 303, data storage module 304.

Instrument Control Interface 302 is a program resident in computer 300 that provides the user interface to module 200. It is used to program the thermal method for the experiment to select any options and to control the instrument, e.g., start and stop experiments, select purge gas flow rates, and select instrument mode: MDSC or standard DSC.

Data Analysis 303 is a program resident in computer 300 that is used to display and process the results of the experiment. The user may select the signals to be displayed and display options such as axis scaling and selection of the abscissa. Analysis of the results may also be performed, such as integration of the area of a peak to determine the enthalpy of a transition.

Data Storage 304 is a non-volatile storage of the experimental results, e.g., a hard disk drive.

Figure 3:
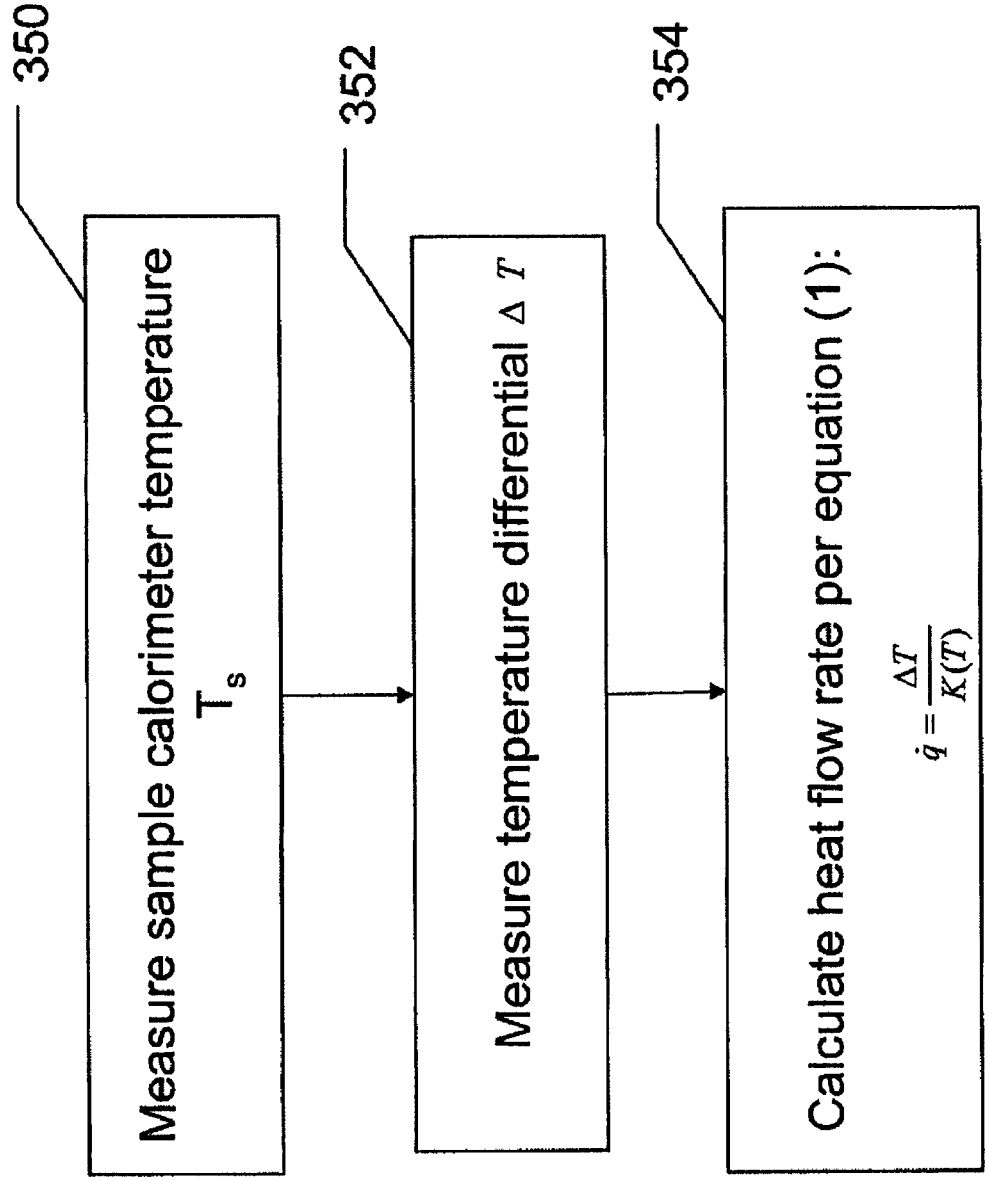
FIG. 3 depicts exemplary steps involved in a method for determining heat flow rate using a DSC sensor according to an embodiment of the present invention.

FIG. 3 is a flow chart of a method for using a DSC sensor 20 to measure heat flow rate using equation (1) according to an embodiment of the present invention. In step 350, the sample calorimeter temperature $T_s$ is measured between wires 8 and 9. In step 352, the differential temperature $\Delta T = T_s - T_r$ is measured between wires 7 and 8. In step 354, the measured sample heat flow rate is calculated as $$\dot{q} = \frac{\Delta T}{K(T)}.$$

The temperature dependent proportionality factor $K(T)$ is typically determined by a DSC manufacturer, and supplied to users. Alternatively, $K(T)$ can be determined by performing heat flow rate measurements using calibration standards such as sapphire whose specific heat capacity is known precisely. The values of $K(T)$ are found that when divided into the differential temperature yield the correct value of the sample heat flow rate. Sample heat flow rate is calculated by multiplying the calibration sample mass by its specific heat capacity and its heating rate.

Figure 4:
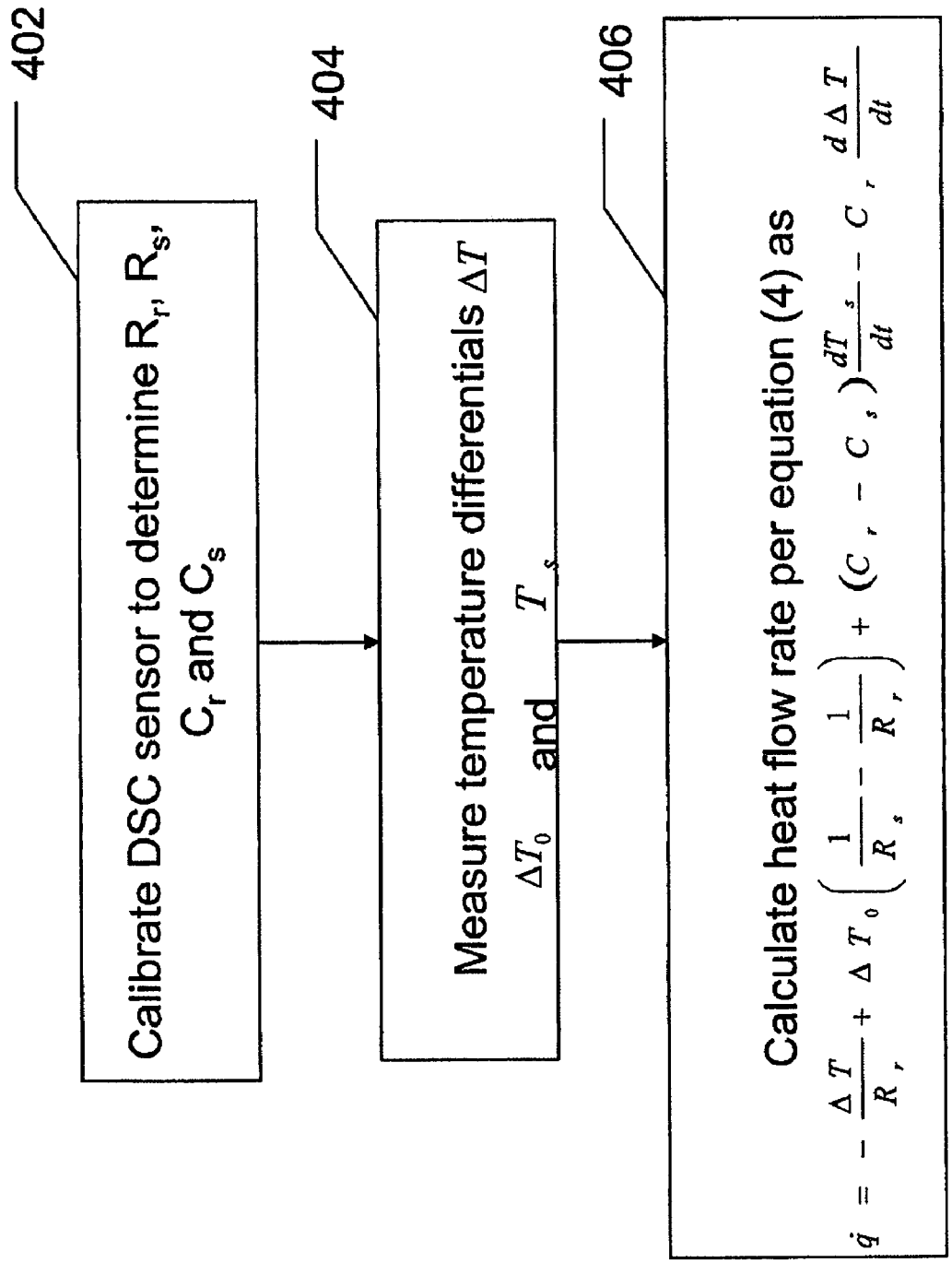
FIG. 4 depicts exemplary steps involved in a method for determining heat flow rate using a DSC sensor according to an embodiment of the present invention.

FIG. 4 is a flow chart of a method for using a DSC sensor 100 to measure heat flow rate using equation (4). In step 402, the USC sensor is calibrated according to the calibration procedure of U.S. Pat. No. 6,431,747 to determine $R_s$, $R_r$, $C_s$, and $C_r$. In step 404, $\Delta T$, $\Delta T_0$ and $T_s$ are measured. $\Delta T = T_s - T_r$, the differential temperature between the sample and reference, is measured between wires 7 and 8. $\Delta T_0 = T_0 - T_s$, the differential temperature between sample platform 6 and base 2, is measured between wires 8 and 10. The sample calorimeter temperature, $T_s$, is measured between wires 8 and 9. In step 406, the measured sample heat flow rate is calculated as $$\dot{q} = -\frac{\Delta T}{R_r} + \Delta T_0 \left( \frac{1}{R_s} - \frac{1}{R_r} \right) + (C_r - C_s) \frac{dT_s}{dt} - C_r \frac{d\Delta T}{dt}.$$

The derivatives, $$\frac{dT_s}{dt} \text{ and } \frac{d\Delta T}{dt}$$

can be determined using numerical methods in a number of well-known ways. For example, the derivative can be calculated according to the equation $$\frac{dx}{dt} = \frac{x(1) - x(0)}{\Delta t}.$$

That is, the derivative at time 1 is the value of x measured at time 1 less the value of measured at time 0 divided by the sampling interval $\Delta t$, wherein x is the value of $T_s$ or $\Delta T$ at the appropriate time. An alternative calculation of the derivative is according to equation $$\frac{dx}{dt} = \frac{x(2) - x(0)}{2\Delta t},$$

wherein the derivative at time 1 is determined by subtracting the value of x at time 0 from the value of x at time 2 and dividing by twice the sampling interval, wherein x is the value of $T_s$ or $\Delta T$ at the appropriate time. In the preferred embodiment, the derivatives with respect to time of $T_s$ and $\Delta T$ are calculated, for example, using an 11 point quadratic Savitzky-Golay numerical derivative. The Savitzky-Golay numerical derivative is described in A. Savitzky and M. J. E. Golay, (July 1964) V 36 no. 8, 1627, Analytical Chemistry.

Figure 5:
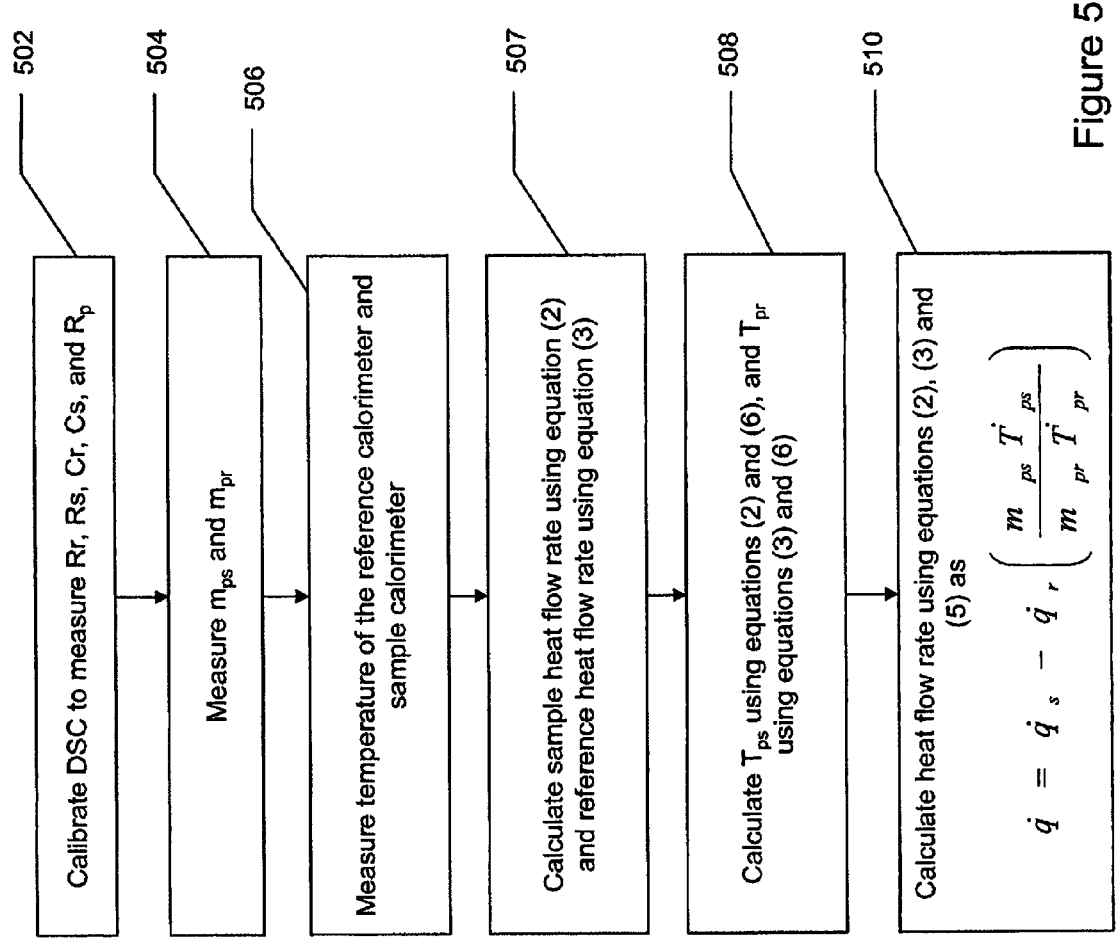
FIG. 5 depicts exemplary steps involved in a method for determining heat flow rate using a DSC sensor according to an embodiment of the present invention.

FIG. 5 is a flow chart of a method for using a DSC sensor 100 to measure heat flow rates using equations (2), (3), (5), (6) and (7). In step 502, DSC sensor 100 is calibrated as described in Danley to determine, $R_s$, $R_r$, $C_s$, and $C_r$. In step 504, the mass of the sample container, $m_{ps}$, and the mass of the reference container, $m_{pr}$, are weighed. In step 506, the temperature of the sample calorimeter is measured between wires 8 and 9, and the temperature of the reference calorimeter is obtained as $T_r = T_s - \Delta T$. In step 507, the sample heat flow rate, $\dot{q}_s$, is calculated using equation (2), and the reference heat flow rate, $\dot{q}_r$, is calculated using equation (3). In step 508, the temperature of the sample container is calculated using equations (2) and (6), $T_{ps} = T_s - \dot{q}_s R_p$, and the temperature of the reference container is calculated using equations (3) and (7), $T_{pr} = T_r - \dot{q}_r R_p$. In step 510, the heat flow rate calculated using equations (2), (3), and (5) as $$\dot{q} = \dot{q}_s - \dot{q}_r \left( \frac{m_{ps} \dot{T}_{ps}}{m_{pr} \dot{T}_{pr}} \right).$$

The required derivatives $\dot{T}_{ps}$ and $\dot{T}_{pr}$ can be calculated using the numerical methods described above for the values of the $T_{ps}$ and $T_{pr}$ at the appropriate times.

When using the improved heat flow calculation method, the sample and reference heat flows are measured separately, and the reference heat flow is multiplied by a factor that is the product of the ratio of pan masses and the ratio of the pan heating rates. The pan mass and heating rate corrected reference heat flow is subtracted from the sample heat flow. To obtain optimal results, two problems relating to the generation of noise must be addressed. In accordance with additional embodiments of the present invention, the form of the heat flow calculation performed in step 510 is modified to account for noise problems, as discussed below and also in U.S. Pat. No. 6,488,406 (which is incorporated by reference herein in its entirety except for column 25, lines 34-35, which should read "In the numerator, the difference between sample and reference pan heating rates cancels the correlated noise.").

The first problem occurs when very low heating rates are used. The derivatives of the pan temperatures, i.e. the pan heating rates $dT_{ps}/dt$ and $dT_{pr}/dt$, are computed numerically using several data points either side of the evaluation point. Preferably, a technique developed by A. Savitsky and N. J. B. Golay, "Smoothing and Differentiation by Simplified Least Squares Procedures," Analytical Chemistry, Vol. 36, No. 8, pp. 1627-1639 (which is incorporated by reference herein) is used to obtain a least squares polynomial fit of the data to be differentiated (in this case temperatures or temperature differences). However, numerical differentiation is well known to create a noisy signal. At low heating rates, such as 0.1° C./min, the temperature changes very slowly and because of the limited resolution of temperature measurement and, the measured temperature often backs up. When that happens, the calculated derivatives often become very close to zero or negative. When the derivative of reference pan temperature in the denominator of the pan heating rate ratio is very close to zero, we have a "near divide by zero" and the factor multiplying the reference heating rate becomes very large (either negative or positive) and the calculated heat flow shows huge spikes.

This problem cannot be resolved simply by smoothing the derivatives, because if the transition peaks are smoothed, then improvement in resolution of the invention is lost. In an embodiment of the present invention, this problem is preferably resolved by taking advantage of the observation that the noise in the sample and reference pan derivatives is very well correlated.

The derivative of the reference pan temperature is added and subtracted from the numerator:

$$\frac{\frac{dT_{ps}}{dt}}{\frac{dT_{pr}}{dt}} = \frac{\frac{dT_{ps}}{dt} - \frac{dT_{pr}}{dt} + \frac{dT_{pr}}{dt}}{\frac{dT_{pr}}{dt}}$$

Then this equation is rearranged to give:

$$\frac{\frac{dT_{ps}}{dt}}{\frac{dT_{pr}}{dt}} = 1 + \frac{\frac{dT_{ps}}{dt} - \frac{dT_{pr}}{dt}}{\frac{dT_{pr}}{dt}}$$

In the numerator, the difference between sample and reference pan heating rates cancels the correlated noise. Because the sample and reference sides of the DSC are independent, and as long as the reference is transition free, the heating rate of the reference pan is always very close to the programmed heating rate. Replace the reference pan heating rate in the denominator with the programmed heating rate:

$$\frac{\frac{dT_{ps}}{dt}}{\frac{dT_{pr}}{dt}} = 1 + \frac{\frac{dT_{ps}}{dt} - \frac{dT_{pr}}{dt}}{b}$$

where b is the programmed heating rate. The heat flow spikes that result from the near zero denominator are thus eliminated, and the correlated sample and reference pan heating rate noise is cancelled. In accordance with an embodiment of the present invention, the sample heat flow equation used in step 510 then becomes:

$$q_{ss} = q_s - q_r \cdot \frac{m_{ps}}{m_{pr}} \left( 1 + \frac{\frac{dT_{ps}}{dt} - \frac{dT_{pr}}{dt}}{b} \right).$$

Another problem that occurs during transitions is also preferably resolved as follows. The sample and reference heat flows both have a rather high level of noise that is common mode, i.e. it is essentially identical in both signals and can be eliminated by taking the difference between the two signals. During the baseline portion of a DSC experiment, the sample and reference pan heating rates are essentially identical and equal to the programmed heating rate so that the heating rate correction term applied to the reference heat flow is 1. Under these conditions, the common mode noise in the sample and reference heat flows cancels and a low noise heat flow signal is obtained. When a transition occurs, the heating rate correction term becomes substantially larger than 1. The noise in the reference heat flow signal is increased by this gain factor and cancellation of the common mode noise is lost. Hence, during a transition, the resultant sample heat flow $q_{ss}$ becomes very noisy.

This problem can also be resolved. The second term on the right hand side of the heat flow equation involving the reference heat flow is expanded, giving $$q_{ss} = q_s - q_r \cdot \frac{m_{ps}}{m_{pr}} - q_r \cdot \frac{m_{ps}}{m_{pr}} \cdot \frac{\frac{dT_{ps}}{dt} - \frac{dT_{pr}}{dt}}{b}$$

So far nothing has been gained, but because the sample and reference sides of the DSC sensor are independent, the reference heat flow (generally, just that of an empty pan) changes very slowly with time and smoothing or filtering may be applied without effecting the reference heat flow. Thus, in accordance with an embodiment of the present invention, the reference heat flow in the third term of the equation above is smoothed, or filtered so that it is quiet. The resulting equation used in step 510 is $$q_{ss} = q_s - q_r \cdot \frac{m_{ps}}{m_{pr}} - \overline{q_r} \cdot \frac{m_{ps}}{m_{pr}} \cdot \frac{\frac{dT_{ps}}{dt} - \frac{dT_{pr}}{dt}}{b}$$

The over bar on the second reference heat flow term indicates that it is smoothed or filtered. With this configuration, the common mode noise in the sample heat flow is cancelled by that of the first reference heat flow term. During the baseline part of an experiment, the third term is zero because the sample and reference pan heating rates are identical. Then, during a transition, when the pan heating rates differ, the gain of the heating rate term is applied to a smoothed or filtered reference heat flow. In this way, a quiet heat flow signal is obtained at all times during an experiment, with no loss of resolution because of smoothing or filtering.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, claims directed to the method and/or process of the present invention should not be limited to the performance of their steps in the order written, and one skilled in the art can readily appreciate that the sequences may be varied and still remain within the spirit and scope of the present invention.

What is claimed is:

1. A differential scanning calorimeter sensor, comprising:
a base having a relatively thick lower portion and a sample thin wall part and a reference thin wall part that are each attached to the relatively thick lower portion;
a sample platform joined to the base on a top portion of the sample thin wall part, the sample platform configured to support a sample container on a first side of the sample platform;
a reference platform joined to the base on a top portion of the reference thin wall part, the reference platform configured to support a reference container on a first side of the reference platform;
a sample thermocouple wire attached to the sample platform on a second side of the sample platform opposite the first side of the sample platform, the sample thermocouple configured to measure the temperature of a sample;
a reference thermocouple wire attached to the reference platform on a second side of the reference platform opposite the first side of the reference platform, the reference thermocouple configured to measure the temperature of a reference;
a first base thermocouple wire attached to the base; and
a second base thermocouple wire attached to the base,
wherein the relatively thick lower portion of the base, the sample thin wall part, the reference thin wall part, and the first base thermocouple wire are made from a first alloy of a thermocouple pair having a first alloy and a second alloy, and
wherein the reference platform, the sample platform, the sample thermocouple wire, the reference thermocouple wire, and the second base thermocouple wire are made from a second alloy of the thermocouple pair,
wherein a sample thermocouple junction is formed between the sample platform and the sample thin wall part,
wherein a reference thermocouple junction is formed between the reference platform and the reference thin wall part,
wherein all heat that flows between the sample container and base flows across the sample thermocouple junction, and
wherein all heat that flows between the reference container and base flows across the reference thermocouple junction.

2. The differential scanning calorimeter sensor recited in claim 1, wherein the sample and reference thin walls parts have a cylindrical shape.

3. The differential scanning calorimeter sensor recited in claim 1, wherein the sample and reference platforms are joined to the sample cylindrical thin wall part and reference cylindrical thin wall part, respectively, of the base using diffusion bonding.

4. The differential scanning calorimeter sensor recited in claim 1, wherein the reference container contains a reference material.

5. The differential scanning calorimeter sensor recited in claim 4, wherein one alloy of the thermocouple pair is chromel, and the other alloy of the thermocouple pair is constantan.

6. A sensor for use in a differential calorimeter, comprising:
a base;
a sample platform joined to the base for supporting a sample container, such that a temperature program can be applied to the sample container through the sample platform;
a reference platform joined to the base for supporting a reference container, such that the temperature program can be applied to the reference container through the sample platform; and
at least one thermocouple attached to the sensor in a region that is external to an area of thermal contact between the sensor and one or more of the sample and reference containers, wherein the sensor is configured to measure one or more differential temperatures externally to the area of thermal contact,
wherein the base comprises:
a relatively thick lower portion;
a sample cylindrical thin wall part, extending from the lower portion of the base and upon which the sample platform is supported;
a reference cylindrical thin wall part, extending from the lower portion of the base and upon which the reference platform is supported;
wherein a sample thermocouple junction is formed between the sample platform and the sample cylindrical thin wall part,
wherein a reference thermocouple junction is formed between the reference platform and the reference cylindrical thin wall part,
wherein all heat that flows between the sample container and base flows across the sample thermocouple junction, and
wherein all heat that flows between the reference container and base flows across the reference thermocouple junction.

7. A differential scanning calorimeter, comprising:
a cell module that includes a sensor assembly and heating element configured to heat the sensor assembly;
a DSC module that includes a plurality of amplifiers each configured to receive input from a respective thermocouple attached to the sensor assembly and configured to output a signal related to the thermocouple input, the DSC module further including a processor configured to receive the respective outputs from each of the plurality of amplifiers; and
a computer coupled to the processor in the DSC module and configured to perform one or more of programming a thermal method used for an experiment in the differential scanning calorimeter, controlling stopping and starting of experiments, selecting gas purge flow rates, and selecting an instrument mode,
wherein the differential scanning calorimeter is configured to measure a differential temperature using a sample thermocouple wire and reference thermocouple wire that are each attached to the sensor assembly in respective regions that are external to an area of thermal contact between the sensor assembly and respective sample and reference containers,
wherein the sensor assembly comprises:
a base having a sample thin wall part and a reference thin wall part;
a sample platform joined to the base for supporting a sample container on a first side of the sample platform, such that a temperature program can be applied to the sample container through the sample platform;
a reference platform joined to the base for supporting a reference container on a first side of the reference platform, such that the temperature program can be applied to the reference container through the reference platform,
wherein a sample thermocouple junction is formed between the sample platform and the sample thin wall part,
wherein a reference thermocouple junction is formed between the reference platform and the reference thin wall part,
wherein all heat that flows between the sample container and base flows across the sample thermocouple junction,
wherein all heat that flows between the reference container and base flows across the reference thermocouple junction.

8. The differential scanning calorimeter sensor recited in claim 7, wherein the plurality of amplifiers comprises:
a first amplifier configured to receive a signal from the first base thermocouple wire and second base thermocouple wire;
a second amplifier configured to receive a signal from the sample thermocouple wire and the reference thermocouple wire; and
a third amplifier configured to receive a signal from the sample thermocouple wire and the second base thermocouple wire,
wherein the differential scanning calorimeter is configured to measure a base temperature $T_0$, a sample to reference differential temperature $\Delta T$, and a differential temperature $\Delta T_0$ based on outputs from the first, second and third amplifiers, respectively.

9. The differential scanning calorimeter recited in claim 7, wherein the processor in the DSC module comprises:
a thermocouple lookup program that converts the digital signal representing the output signal of the $T_0$ thermocouple to a temperature;
a thermocouple lookup program that converts the digital signal representing the output signal of the $\Delta T$ and $\Delta T_0$ thermocouples to differential temperatures;
a sensor coefficients program that supplies the sensor coefficients used for calculation of heat flow;
a contact resistance model program that calculates a pan contact thermal resistance using a thermal contact thermal resistance model equation;
a heat flow calculator program that calculates heat flow rate;
a temperature control program that determines the power to be supplied to the DSC heating element;
a temperature control program; and
a temporary memory configured to store the results of an experiment during the experiment.

10. The differential scanning calorimeter recited in claim 7, wherein the computer comprises:
an instrument control interface program that provides a user interface to the DSC module;
a data analysis program used to display and process results of an experiment conducted in the differential scanning calorimeter; and
a data storage component comprising non-volatile storage for storing the experimental results.

11. The differential scanning calorimeter recited in claim 7, wherein the sensor assembly further comprises:

a sample thermocouple wire attached to the sample platform on a second side opposite to the first side of the sample platform;

a reference thermocouple wire attached to the reference platform on a second side opposite to the first side of the reference platform;

a first base thermocouple wire attached to the base; and a second base thermocouple wire attached to the base, wherein the base, the sample thin wall part, the reference thin wall part, and the first base thermocouple wire are made from a first alloy of a thermocouple pair having a first alloy and a second alloy, and wherein the reference platform, the sample platform, the sample thermocouple wire, the reference thermocouple wire, and the second base thermocouple wire are made from a second alloy of the thermocouple pair.

12. The differential scanning calorimeter recited in claim 11, wherein one alloy of the thermocouple pair is chromel, and the other alloy of the thermocouple pair is constantan.

* * * * *